US00PP37341P3

(12) United States Plant Patent
Adams

(10) Patent No.: US PP37,341 P3
(45) Date of Patent: Mar. 24, 2026

(54) RASPBERRY PLANT NAMED 'PS-12.082-54'

(50) Latin Name: *Rubus idaeus*
Varietal Denomination: PS-12.082-54

(71) Applicant: Plant Sciences, Inc., Watsonville, CA (US)

(72) Inventor: Scott W. Adams, Carmel Valley, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 19/175,880

(22) Filed: Apr. 10, 2025

(65) Prior Publication Data

US 2025/0338782 P1 Oct. 30, 2025

Related U.S. Application Data

(60) Provisional application No. 63/638,749, filed on Apr. 25, 2024.

(51) Int. Cl.
*A01H 5/08* (2018.01)
*A01H 6/74* (2018.01)

(52) U.S. Cl.
USPC ..... Plt./204
CPC ..... *A01H 6/7499* (2018.05); *A01H 5/08* (2013.01)

(58) Field of Classification Search
USPC ..... Plt./204
See application file for complete search history.

(56) References Cited

U.S. PATENT DOCUMENTS

| | | | |
|---|---|---|---|
| PP27,582 | P3 | 1/2017 | Adams |
| PP27,583 | P3 | 1/2017 | Adams |
| PP31,716 | P3 | 5/2020 | Adams |

*Primary Examiner* — Shubo Zhou
*Assistant Examiner* — Zachariah Allan Kay
(74) *Attorney, Agent, or Firm* — Foley & Lardner LLP

(57) ABSTRACT

This invention relates to a new and distinct everbearing variety of raspberry plant named 'PS-12.082-54'. The new variety is primarily adapted to the growing conditions of the central coast of California and is characterized by the following: mid-season primocane production with medium sized fruit of strong yellow orange coloration. Fruit is of consistent conic shape, releases easily from receptacle, is very glossy and possesses an average % brix of 10.2. Foliage is flat, medium green; possessing weak rugosity, weak gloss and mostly 3 foliates. Primocanes have an absent or very weak waxy coat, medium prickle density of small green prickles and are absent of anthocyanin coloration.

5 Drawing Sheets

Latin name of the genus and species of the plant claimed: *Rubus idaeus*.

Variety denomination: 'PS-12.082-54'.

BACKGROUND OF THE INVENTION

The present invention relates to a new and distinct fall-bearing raspberry variety designated as 'PS-12.082-54'. This new variety is a result of a controlled cross made in 2012 in Watsonville, California between raspberry variety 'BOUNTIFUL' (patented, U.S. Plant Pat. No. 27,582) as the female parent and raspberry variety 'PARAGON' (patented, U.S. Plant Pat. No. 27,583) as the male parent in an ongoing breeding program. The variety is botanically known as *Rubus idaeus* and was tested as 'RR 12.082-54' and 'PS-8254'.

The seedling resulting from the aforementioned cross was asexually propagated by dormant canes in Santa Cruz County, California and was subsequently selected by the inventor from a controlled breeding plot in Watsonville, California in 2014. After its selection, the new variety was further asexually propagated by dormant canes, roots and non-dormant root shoot cuttings in Watsonville (Santa Cruz County), Manteca (San Joaquin County), and Macdoel (Siskiyou County), California. The new variety was then extensively tested over the next several years in fruiting fields in Watsonville, California. This propagation has demonstrated that the combination of traits disclosed herein as characterizing the new variety are fixed and remain true to type through successive generations of asexual reproduction.

BRIEF SUMMARY OF THE INVENTION

'PS-12.082-54' is primarily adapted to the climate and growing conditions of the central coast of California. This region provides the necessary year-round temperatures required for it to produce a healthy plant stand and to remain in fruit production from July through November on primocanes and in the ensuing year from May through July on the floricanes. Damage to fruit and young leaves has been observed in summer temperatures at or above 95° F. (35° C.). No winter damage has been observed on fruiting plants in off-cycle (winter) production regions of USDA climate zones 9b and above. No winter damage has been observed on dormant plants in on-cycle (summer) production regions of USDA climate zones 7b-9b. In climate zones below this, winter hardiness is unknown for 'PS-12.082-54'. 'PS-12.082-54' is not drought tolerant and requires frequent irrigation to maintain proper plant health. The following traits have been repeatedly observed and are determined to be unique characteristics of 'PS-12.082-54', which in combination distinguish this raspberry plant as a new and distinct variety:

1. Strong yellow green prickles.
2. High fruit yield.
3. Strong orange yellow fruit.
4. Absent to very weak primocane glaucosity.
5. Avg % Brix of 10.2.

The raspberry variety that is believed to be most closely related to the new raspberry variety 'PS-12.082-54' is the raspberry variety 'MAJESTIC' (patented, U.S. Plant Pat. No. 31,716). In comparison to the similar raspberry variety 'MAJESTIC', 'PS-12.082-54' differs by the following combination of characteristics described in Table 1:

Comparison Between 'PS-12.082-54' and 'Majestic'

TABLE 1

| Characteristic | 'PS-12.082-54' | 'MAJESTIC' (US PP31,716) |
|---|---|---|
| Prickle coloration (tip) | RHS N144D Strong yellow green | RHS N186B Dark greyish purple |
| Leaf shape (cross section) | Flat | Slightly convex |
| Rugosity | Weak | Medium |
| Color mature fruit | RHS 17A Strong orange yellow | RHS 53A Vivid reddish orange |
| Relative size of drupes | Large | Medium |
| Predominant shape of fruit | Conical | Conical |
| Peduncle anthocyanin intensity | Absent | Absent to very weak |
| Relative number of pedicel prickles | 19.6 Medium | 22.1 Many |

'PS-12.082-54' differs from its parents, 'BOUNTIFUL' and 'PARAGON' by the following combination of characteristics described in Table 2:

Comparison Between 'PS-12.082-54', 'Bountiful', and 'Paragon'

TABLE 2

| Characteristic | 'PS-12.082-54' | 'BOUNTIFUL' (US PP27,582) | 'PARAGON' (US PP27,583) |
|---|---|---|---|
| Productivity | High | High | Medium |
| Crates/acre (18-mo.) | 10,892 | 10,476 | 7,222 |
| Color mature fruit | RHS 17A Strong yellow orange | RHS 34A Vivid reddish orange | RHS 34A Vivid reddish orange |
| Glossiness (fruit) | Very high | Medium | High |
| Firmness (fruit) | High | High | Very high |
| Adherence of receptacle | Weak | Very weak | Medium |
| Primocane time of fruiting | Medium | Late | Early |
| Relative size of drupelet | Large | Medium | Small |
| Primocane fruit weight (g) | 4.1 | 4.6 | 4.2 |
| Soluble solids (% brix) | 10.2 | 9.8 | 11.6 |

For identification, a series of molecular markers have been determined for this new variety.

BRIEF DESCRIPTIONS OF THE DRAWINGS

The accompanying color photographs illustrate the overall appearance of typical specimens of the new raspberry variety 'PS-12.082-54' at various stages of development as true as reasonably possible with color reproductions of this type. Color in the photographs may differ slightly from the color value cited in the detailed botanical description which accurately describes the color of 'PS-12.082-54'. The depicted plant and plant parts of the new raspberry variety 'PS-12.082-54' were taken in Watsonville, California and are approximately 2 to 16 months old:

DETAILED BOTANICAL DESCRIPTION

Figure 1:
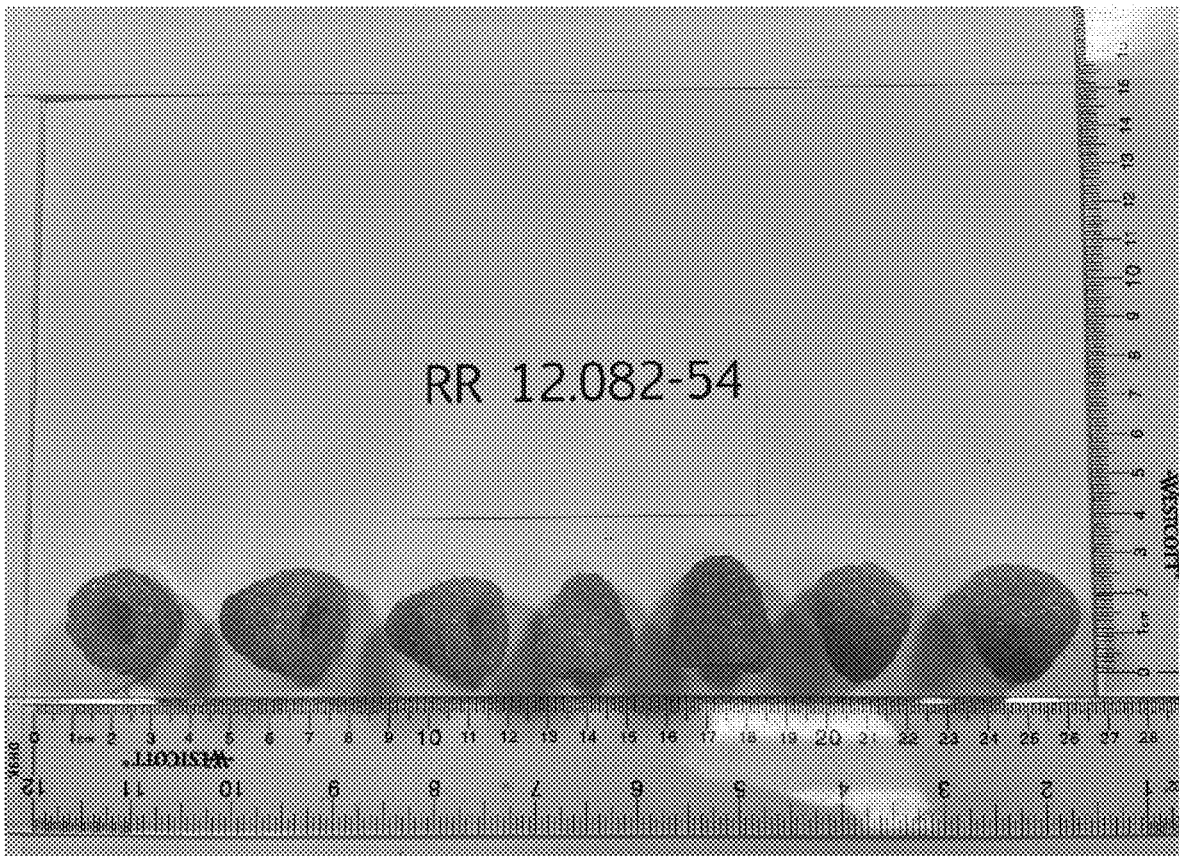
FIG. 1 shows typical primocane fruit shape, color and gloss characteristics of 'PS-12.082-54' taken in the month of August 2024.
Figure 2:
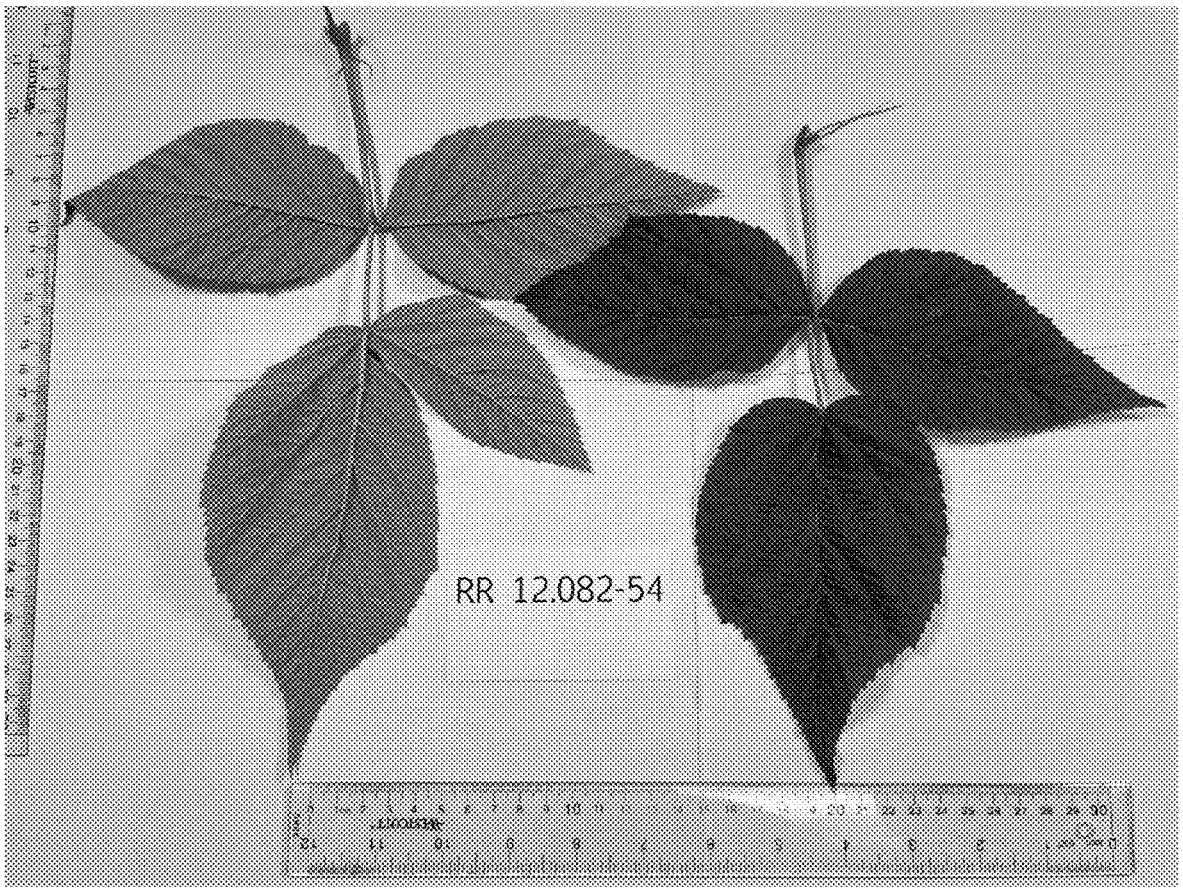
FIG. 2 shows typical shape, gloss, coloration, foliate and rugosity characteristics of 'PS-12.082-54' taken in the month of August 2024.
Figure 3:
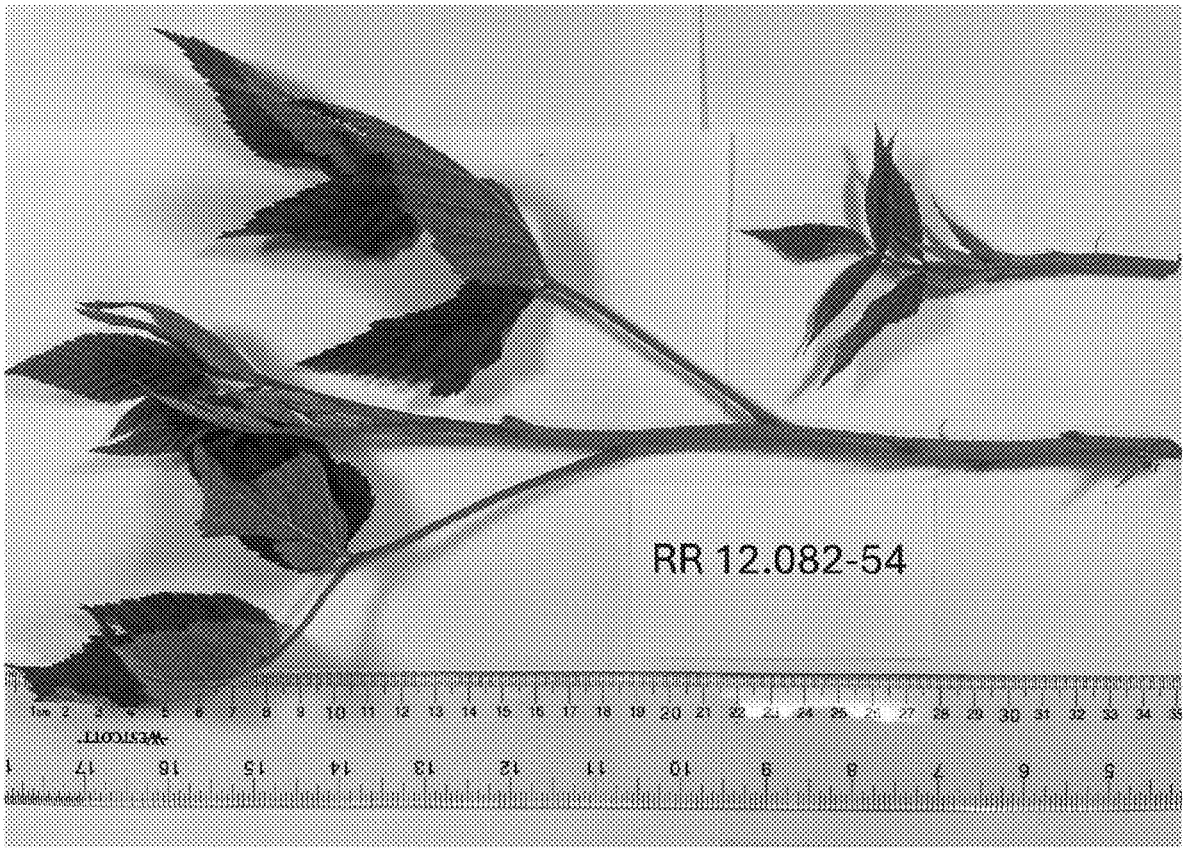
FIG. 3 shows typical young shoot characteristics of 'PS-12.082-54' taken in the month of March 2025.
Figure 4:
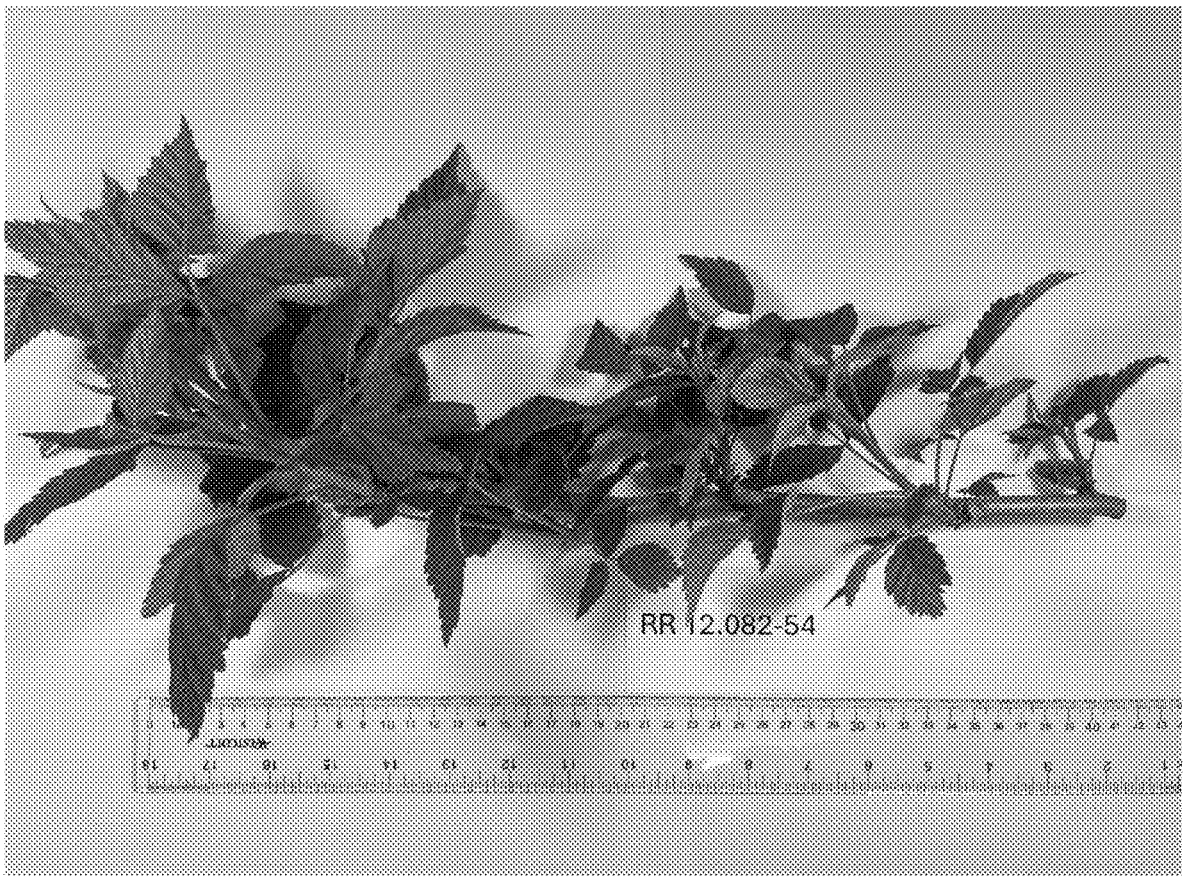
FIG. 4 shows typical floricane characteristics of 'PS-12.082-54' taken in the month of March 2025.
Figure 5:
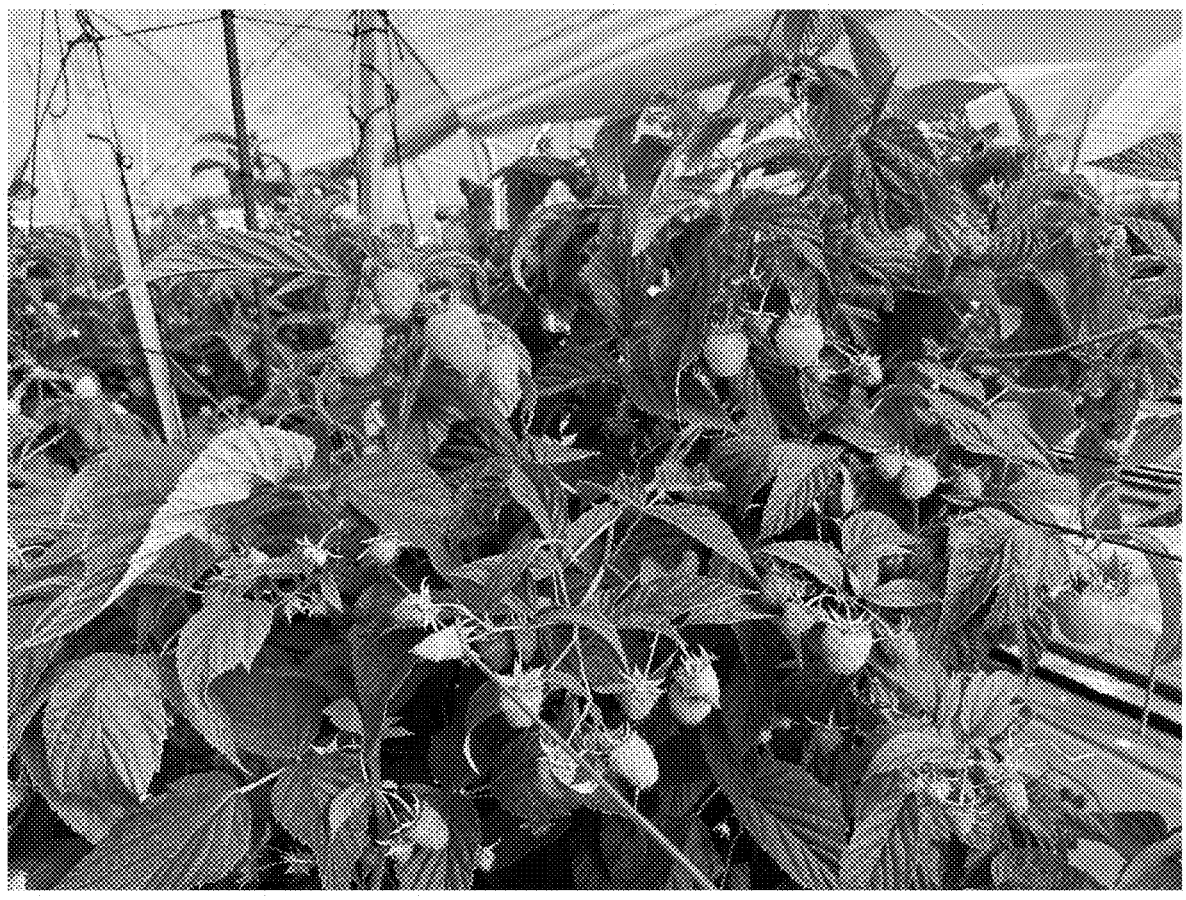
FIG. 5 shows typical floricane characteristics of 'PS-12.082-54' taken in the month of May 2022.

'PS-12.082-54' has not been observed under all possible environmental conditions. The characteristics of the new variety may vary in detail, depending upon variations in environmental factors, including weather (temperature, humidity and light intensity), day length, soil type, and location.

The aforementioned photographs, together with the following description of the new raspberry variety 'PS-12.082-54', unless otherwise noted, are based upon observations taken during the 2023-2024 growing season in Watsonville, California. Primocane measurements and ratings were taken from plants of 'PS-12.082-54' dug from a nursery located in Siskiyou County, California during the middle of October 2022 and planted approximately 3 to 4 weeks later in Watsonville, California. The approximate age of the observed primocane plants is 7 to 8 months. Floricane measurements and ratings were taken from the same planting of 'PS-12.082-54' at an approximate age of 16 to 18 months. Yield observations and fruit quality characteristics are averaged from 3 years of data collected from the 2021 through 2024 production seasons. Flower measurements and characteristics are from secondary flowers unless otherwise noted. Fruit characteristics and measurements are from secondary fruit unless otherwise noted. Foliage characteristics and measurements are from 3-foliate foliage unless otherwise noted.

Color terminology where noted follows The R.H.S. Colour Chart Sixth Edition, Royal Horticultural Society, London, United Kingdom (2015).

The following Tables 3-7 describe fruit, plant, foliage, flower and pest/disease characteristics of the new raspberry 'PS-12.082-54' in comparison to the similar raspberry variety 'MAJESTIC' (patented, U.S. Plant Pat. No. 31,716).

Comparison Between 'PS-12.082-54' and 'Majestic'

TABLE 3

FRUIT CHARACTERISTICS

| Characteristic | 'PS-12.082-54' | 'MAJESTIC' (US PP31,716) |
|---|---|---|
| Color mature fruit | RHS 17A Strong orange yellow | RHS 43A Vivid reddish orange |
| Color achenes | RHS 159A Light yellowish pink | RHS 159A Light yellowish pink |
| Fruit length (mm) | 26.22 | 25.49 |
| Fruit width (mm) | 22.74 | 22.73 |
| Length/width ratio | 1.15 Longer than broad | 1.12 Longer than broad |
| Seed weight (mg) | 1.55 | 1.68 |
| Drupelets per berry | 107 | 131 |
| Weight of single drupe (g/drupe) | 0.066 | 0.044 |
| Drupe length (mm) | 4.44 | 7.15 |
| Drupe diameter (mm) | 4.87 | 4.19 |
| Relative size of drupes | Large | Medium |
| Fruit size | Medium | Medium |
| Fruit per node | 12 | 11 |
| Predominant shape | Conical | Conical |
| Receptacle length (mm) | 24.04 | 23.55 |
| Receptacle diameter (mm) | 10.22 | 10.41 |
| Receptacle color | RHS 155B Pale yellow | RHS 155B Yellowish white |
| Evenness of color (fruit) | Even | Even |
| Glossiness | Very high | High |
| Adherence of receptacle | Weak | Weak |
| Firmness of flesh | Medium | High |
| Firmness of skin | High | High |
| Soluble solids (% brix) | 10.2 | 10.8 |
| Fruit use (intended market) | Fresh market | Fresh market |

TABLE 4

PLANT CHARACTERISTICS

| Characteristic | 'PS-12.082-54' | 'MAJESTIC' (US PP31,716) |
|---|---|---|
| General: | | |
| Habit | Upright | Upright |
| Plant height (m) | 1.4 | 1.8 |
| Plant width (cm) | 31 | 35 |
| Time to initiate roots (days) | 10-12 | 10-12 |
| Canes per hill | 10.5 | 10.4 |
| Productivity | High | High |
| Crates/acre (18-mo.) | 10,892 | 10,490 |
| Self-fruitfulness | Yes | Yes |
| Type of bearing | Everbearing | Everbearing |
| Primocane: | | |
| Color (true) | RHS N144C Strong yellow green | RHS 145A Strong yellow green |
| Length (cm) | 144.2 | 178.1 |
| Basal diameter (mm) | 20.77 | 13.62 |
| Diameter central ⅓ (mm) | 10.98 | 11.38 |
| Lateral length at central ⅓ (cm) | 30.5 | 28.5 |
| No. fruiting laterals per cane | 15.7 | 15.3 |
| Total nodes per cane | 36 | 35 |
| Internode length at central ⅓ (mm) | 44.08 | 39.01 |
| Anthocyanin coloration | n/a | RHS 59B Deep purplish red |
| Anthocyanin intensity | Absent | Absent to very weak |
| Pubescence | Absent | Absent |
| Vegetative bud length (mm) | 6.25 | 10.34 |
| Vegetative bud diameter (mm) | 4.88 | 5.46 |
| Vegetative bud shape | Widely ovate | Ovate |
| Vegetative bud color | RHS 166A Greyish brown | RHS 187B Dark red |
| Strength of waxy coat (glaucosity) | Absent to very weak | Absent to very weak |
| Time of fruiting (First Day) | July 22$^{nd}$ | July 15$^{th}$ |
| Time of fruiting (Last Day) | Nov. 21$^{st}$ | Nov. 22$^{nd}$ |
| Length of fruiting season | 123 Days | 132 Days |
| % of total yield | 69% | 44% |
| Primocane fruit weight (g) | 4.1 | 4.2 |
| Primocane yield (g/plant) | 3,655 | 2,571 |
| Young Shoots: | | |
| Number (per meter) | 20-25 Medium | 15-20 Medium |
| Anthocyanin presence | Absent | Present |

TABLE 4-continued

| PLANT CHARACTERISTICS | | |
|---|---|---|
| Characteristic | 'PS-12.082-54' | 'MAJESTIC' (US PP31,716) |
| Anthocyanin coloration | n/a | RHS 179A Moderate red |
| Anthocyanin intensity | Absent | Medium |
| Prickles: | | |
| Prickle presence | Present | Present |
| Prickle coloration (tip) | RHS N144D Strong yellow green | RHS N186B Dark greyish purple |
| Prickle coloration (base) | RHS N144C Strong yellow green | RHS N186C Dark greyish red |
| Prickle length at central ⅓(mm) | 0.52 | 0.70 |
| Prickle base at central ⅓ (mm) | 0.41 | 1.23 |
| Prickle density per cm at central ⅓ | 5.12 Medium | 5.35 Medium |
| Prickle texture | Rigid | Rigid |
| Attitude of the tip | Horizontal | Horizontal |
| Floricane: | | |
| Color (true) | RHS N167A Brownish orange | RHS 165B Brownish orange |
| Length (cm) | 107.4 | 130.8 |
| Width at central ⅓ (mm) | 9.75 | 10.88 |
| Total nodes per cane | 16 | 20 |
| Internode length at central ⅓ (mm) | 44.77 | 40.70 |
| Fruiting lateral attitude | Erect | Erect |
| Time of fruiting (First Day) | May 16$^{th}$ | May 16$^{th}$ |
| Time of fruiting (Last Day) | July 21$^{st}$ | July 23$^{rd}$ |
| Length of fruiting season | 66 Days | 68 Days |
| % of total yield | 31% | 56% |
| Floricane fruit weight (g) | 4.0 | 4.0 |
| Floricane yield (g/plant) | 1,479 | 3,273 |

TABLE 5

| FOLIAGE CHARACTERISTICS | | |
|---|---|---|
| Characteristic | 'PS-12.082-54' (3 Foliate) | 'MAJESTIC' (US PP31,716) (3 Foliate) |
| General: | | |
| Color of upper surface | RHS NN137B Greyish olive green | RHS 137A Moderate olive green |
| Color of lower surface | RHS 190B Pale green | RHS 192A Pale yellow green |
| Venation | Pinnate | Pinnate |
| Shape in cross section | Flat | Slightly convex |
| Arrangement | Compound | Compound |
| Relief between veins (rugosity) | Weak | Medium |

TABLE 5-continued

| FOLIAGE CHARACTERISTICS | | |
|---|---|---|
| Characteristic | 'PS-12.082-54' (3 Foliate) | 'MAJESTIC' (US PP31,716) (3 Foliate) |
| Glossiness | Weak | Weak |
| Number of leaflets/leaf | Mostly 3 | Equal 3 - 5 |
| Total leaf length (cm) | 23.4 | 21.2 |
| Total leaf width (cm) | 22.8 | 22.1 |
| Terminal Leaflet: | | |
| Length (mm) | 143.9 | 116.2 |
| Width (mm) | 87.4 | 79.1 |
| Length/width ratio | 1.6 Longer than broad | 1.5 Longer than broad |
| Size | Medium | Medium |
| Shape | Cordate | Cordate |
| Shape of base | Rounded | Cordate |
| Shape of tip | Acuminate | Acuminate |
| Margins | Biserrate | Biserrate |
| Lateral Leaflet: | | |
| Length (mm) | 113.8 | 104.9 |
| Width (mm) | 56.8 | 77.2 |
| Length/width ratio | 2.0 Much longer than broad | 1.3 Longer than broad |
| Rachis length (mm) | 36.4 | 43.1 |
| Rachis diameter (mm) | 1.54 | 1.90 |
| Rachis anthocyanin coloration of upper surface | n/a | RHS 184A Greyish red |
| Rachis anthocyanin intensity | Absent | Weak |
| Orientation | Opposite | Opposite |
| Arrangement | Compound | Compound |
| Shape | Ovate | Ovate |
| Overlapping | Free | Overlapping |
| Shape of the base | Oblique | Rounded |
| Shape of the tip | Acuminate | Acuminate |
| Margins | Biserrate | Biserrate |
| Petiole: | | |
| Length (mm) | 73.68 | 61.10 |
| Width (mm) | 2.81 | 4.68 |
| Prickle presence | Yes | Yes |
| Prickle orientation | Erect | Erect |
| Anthocyanin coloration of upper surface | n/a | RHS 180B Moderate red |
| Anthocyanin intensity of upper surface | Absent | Absent to very weak |
| Stipule length (mm) | 8.34 | 10.70 |
| Stipule width (mm) | 0.62 | 0.89 |
| Stipule orientation | Erect | Erect |

TABLE 6

| FLOWER CHARACTERISTICS | | |
|---|---|---|
| Characteristic | 'PS-12.082-54' | 'MAJESTIC' (US PP31,716) |
| Petal color (upper surface) | RHS NN155A Yellowish white | RHS 155C Greenish white |

TABLE 6-continued

FLOWER CHARACTERISTICS

| Characteristic | 'PS-12.082-54' | 'MAJESTIC' (US PP31,716) |
|---|---|---|
| Petal color (lower surface) | RHS NN155A Yellowish white | RHS 155C Greenish white |
| Flower diameter (mm) | 22.24 | 21.22 |
| Petal Length (mm) | 7.71 | 7.46 |
| Petal width (mm) | 3.15 | 3.10 |
| Petal length/ width ratio | 2.44 Much longer than broad | 2.40 Much longer than broad |
| Petal shape in cross section | Flat | Flat |
| Petal shape (overall) | Narrowly spatulate | Narrowly spatulate |
| Petal shape (apex) | Rounded | Rounded |
| Petal shape (base) | Attenuate | Attenuate |
| Petal margin | Entire | Entire |
| Petal texture | Glabrous | Glabrous |
| No. petals/flower | 5.2 | 5.2 |
| No. sepals/flower | 5.2 | 5.4 |
| Sepal length (mm) | 9.26 | 9.70 |
| Sepal width at base (mm) | 5.13 | 5.20 |
| Sepal shape | Widely deltate | Widely deltate |
| Sepal shape (apex) | Acuminate | Acuminate |
| Sepal coloration (upper surface) | RHS 144A Strong yellow green | RHS 144A Strong yellow green |
| Sepal coloration (lower surface) | RHS 144B Strong yellow green | RHS 144B Strong yellow green |
| Sepal margin | Entire | Entire |
| Sepal texture | Slightly pubescent | Slightly pubescent |
| No. stamen/flower | 82 | 95 |
| Filament length (mm) | 5.08 | 5.19 |
| Filament color | RHS 155C Greenish white | RHS 155C Greenish white |
| Pollen quantity | Medium | High |
| Pollen color | RHS 196D Yellowish white | RHS 196D Yellowish white |
| Anther length (mm) | 1.20 | 1.12 |
| Anther diameter (mm) | 0.48 | 0.51 |
| Anther coloration (pre-dehiscence) | RHS 155C Greenish white | RHS 155C Greenish white |
| Anther coloration (post-dehiscence) | RHS 165B Brownish orange | RHS 165B Brownish orange |
| Stigma shape | Lobed | Lobed |
| Stigma length (mm) | 0.11 | 0.10 |
| Stigma diameter (mm) | 0.40 | 0.41 |
| Stigma coloration | RHS 145D Light yellow green | RHS 145D Light yellow green |
| Style length (mm) | 3.09 | 3.10 |
| Style diameter (mm) | 0.40 | 0.40 |

TABLE 6-continued

FLOWER CHARACTERISTICS

| Characteristic | 'PS-12.082-54' | 'MAJESTIC' (US PP31,716) |
|---|---|---|
| Style coloration | RHS 145D Light yellow green | RHS 145D Light yellow green |
| Ovule length (mm) | 1.11 | 1.39 |
| Ovule diameter (mm) | 1.01 | 1.42 |
| Ovule coloration | RHS 145B Light yellow green | RHS 145B Light yellow green |
| Pedicle length (mm) | 20.21 | 20.15 |
| Pedicle diameter (mm) | 1.39 | 1.42 |
| Pedicle anthocyanin coloration | n/a | RHS 181C Moderate red |
| Pedicle anthocyanin intensity | Absent | Absent to very weak |
| Relative number of pedicel prickles | 19.6 Medium | 22.1 Many |
| Peduncle anthocyanin presence | Absent | Present |
| Peduncle anthocyanin coloration | n/a | RHS 184A Greyish red |
| Peduncle anthocyanin intensity | Absent | Absent to very weak |

TABLE 7

PEST AND DISEASE REACTIONS

| Characteristic | 'PS-12.082-54' | 'MAJESTIC' (US PP31,716) |
|---|---|---|
| Spotted wing drosophila (*Drosophila suzukii*) | Susceptible | Susceptible |
| Two spotted spider mite (*Tetranychus urticae*) | Susceptible | Susceptible |
| Grey fruit mold (*Botrytis cinerea*) | Susceptible | Susceptible |
| Powdery mildew (*Podosphaera aphanis* var. *aphonic*) | Moderately susceptible | Moderately susceptible |
| Yellow rust (*Phragmidium rubi-idaei*) | Moderately resistant | Moderately resistant |

I claim:

1. A new and distinct raspberry variety named 'PS-12.082-54', as described and illustrated herein.

* * * * *